(12) United States Patent
Ogasawara

(10) Patent No.: US 11,389,617 B2
(45) Date of Patent: Jul. 19, 2022

(54) SLEEP INDUCTION DEVICE AND SLEEP INDUCTION METHOD

(75) Inventor: Masahiro Ogasawara, Osaka (JP)

(73) Assignee: Mignon Bell Co., Ltd., Osaka (JP)

( * ) Notice: Subject to any disclaimer, the term of this patent is extended or adjusted under 35 U.S.C. 154(b) by 22 days.

(21) Appl. No.: 13/499,694

(22) PCT Filed: Dec. 13, 2010

(86) PCT No.: PCT/JP2010/007242
§ 371 (c)(1),
(2), (4) Date: Mar. 31, 2012

(87) PCT Pub. No.: WO2011/070794
PCT Pub. Date: Jun. 16, 2011

(65) Prior Publication Data
US 2012/0310038 A1    Dec. 6, 2012

(30) Foreign Application Priority Data

Dec. 11, 2009    (JP) .............................. JP2009-282313

(51) Int. Cl.
A61M 21/02    (2006.01)
A61N 5/06    (2006.01)
A61M 21/00    (2006.01)

(52) U.S. Cl.
CPC ..... A61M 21/02 (2013.01); *A61M 2021/0044* (2013.01); *A61N 2005/063* (2013.01); *A61N 2005/0651* (2013.01)

(58) Field of Classification Search
CPC . A61B 5/00; A61B 5/05; A61M 21/00; A61N 5/06; G01B 9/00; G02B 1/10; G02B 27/02; F21V 9/00; G01R 31/00
(Continued)

(56) References Cited

U.S. PATENT DOCUMENTS 5,259,830 A * 11/1993 Masuda .......................... 600/27
5,265,598 A * 11/1993 Searfoss ............... A61M 21/00
                                                              600/27
(Continued)

FOREIGN PATENT DOCUMENTS

JP    2007044201 A  *  2/2007
JP    2007-294143 A    8/2007
(Continued)

OTHER PUBLICATIONS

How Many? A Dictionary of Units of Measurement © Russ Rowlett and the University of North Carolina at Chapel Hill 2012 by Russ Rowlett and the University of North Carolina at Chapel Hill On line.*
(Continued)

*Primary Examiner* — Jennifer Pitrak McDonald
*Assistant Examiner* — Sana Sahand
(74) *Attorney, Agent, or Firm* — Ogilvie Law Firm

(57) ABSTRACT

Disclosed is a sleep induction device which exhibits excellent hypnotic effects using light rather than ultrasonic waves or electrical voltages to induce sleep. When the face of a patient is irradiated with diffused ultra narrow band light having a FWHM of 10 nm or less, the specified wavelength of light has excellent hypnotic effects. The sleep induction device is provided with: an ultra narrow band light irradiation means which generates a blue to green ultra narrow band light having a FWHM of 10 nm or less and a peak wavelength range of 430-550 nm; and a diffusion means for reducing the illumination intensity of the light irradiated from the ultra narrow band light irradiation means onto the skin surface of the face to 1-300 lux, and expanding the emission area to the entire face. The green ultra narrow band light has a sleep-inducing effect, and the blue one has a stronger sleep-inducing effect.

10 Claims, 2 Drawing Sheets

(58) Field of Classification Search
USPC ............ 600/310, 407, 27, 300; 607/93, 88; 356/124; 359/584; 362/231
See application file for complete search history.

(56) References Cited

U.S. PATENT DOCUMENTS

| | | | |
|---|---|---|---|
| 5,289,114 A * | 2/1994 | Nakamura et al. ............. | 324/96 |
| 6,623,512 B1 * | 9/2003 | Heller ................... | A61M 21/00 128/898 |
| 6,669,627 B1 * | 12/2003 | Campbell et al. ............. | 600/27 |
| 6,967,791 B2 * | 11/2005 | Schmidtke et al. .......... | 359/806 |
| 7,414,714 B2 * | 8/2008 | Platt et al. .................... | 356/124 |
| 7,570,984 B2 * | 8/2009 | Katsuda et al. ............. | 600/407 |
| 7,722,212 B2 * | 5/2010 | Searfoss ....................... | 362/231 |
| 8,180,419 B2 * | 5/2012 | Debreczeny et al. ........ | 600/310 |
| 2001/0056293 A1 * | 12/2001 | Brainard ........................ | 607/88 |
| 2002/0080493 A1 * | 6/2002 | Tsai et al. ..................... | 359/584 |
| 2003/0069616 A1 * | 4/2003 | Skene ................... | A61M 21/00 607/88 |
| 2003/0187486 A1 * | 10/2003 | Savage, Jr. .......... | A61N 5/0618 607/89 |
| 2004/0138726 A1 * | 7/2004 | Savage, Jr. .......... | A61N 5/0621 607/88 |
| 2006/0184214 A1 * | 8/2006 | McDaniel ....................... | 607/89 |
| 2007/0083079 A1 * | 4/2007 | Lee et al. ........................ | 600/27 |
| 2007/0118026 A1 * | 5/2007 | Kameyama et al. ......... | 600/300 |
| 2007/0233209 A1 * | 10/2007 | Whitehurst ..................... | 607/93 |
| 2007/0282159 A1 * | 12/2007 | Sato et al. ...................... | 600/27 |
| 2008/0103561 A1 * | 5/2008 | Moscovici ...................... | 607/88 |

FOREIGN PATENT DOCUMENTS

| | | |
|---|---|---|
| JP | 2007-299714 A | 11/2007 |
| JP | 2008-245836 A | 10/2008 |
| WO | WO 2008084764 A1 * | 7/2008 |

OTHER PUBLICATIONS

Cajochen et al, Evening exposure to blue light stimulates the expression of the clock gene PER2 in humans, European Journal of Neuroscience, vol. 23, pp. 1082-1086, 2006.*

Thapan et al, An action spectrum for melatonin suppression: evidence for a novel non-rod, non-cone photoreceptor system in humans, Journal of Physiology (2001), 535.1, pp. 261-267.*

* cited by examiner

SLEEP INDUCTION DEVICE AND SLEEP INDUCTION METHOD

TECHNICAL FIELD

The present invention relates to a sound sleep inducing apparatus and a sound sleep inducing method which leads people to sound sleep by diffusing ultra-narrow band light in blue to green having a half bandwidth of 10 nm or less and projecting the light to the entire face of a person.

BACKGROUND ART

A sound sleep inducing apparatus using an ultrasonic wave (Patent Document 1, for example), a sound sleep inducing apparatus which leads people to sound sleep by using an a wave and a ⊖ wave emitted from a light emitting body (Patent Document 2, for example), and a relaxation assisting apparatus which applies a negative voltage and relaxes a human body (Patent Document 3, for example) have been known as apparatuses for inducing sleep or giving relaxation effects.

The inventor is a doctor and has been practicing provision f information and consulting relating to aesthetic dermatologic treatment. The inventor has been keenly examining a skin care method which does not cause a trouble in the skin even after a long use and can obtain safe and sufficient effects in short time through the practice.

[Patent Document 1] JP 2003-199831 A
[Patent Document 1] JP 1996-229131 A
[Patent Document 1] JP 2002/028464 A1

DISCLOSURE OF THE INVENTION

Problems to be Solved by the Invention

The inventor has obtained finding that, in a beauty clinic managed by himself, if an ultra-narrow band light having a half bandwidth of 10 nm or less is diffused and projected to the face of a subject, light having a specific wavelength has an excellent hypnotic effect. Moreover, the inventor was convinced through experiments that the hypnotic effect is excellent and cannot be obtained by usual light having a wider half bandwidth. The invention has an object to provide a sound sleep inducing apparatus and a sound sleep inducing method with a high hypnotic effect without using ultrasonic waves or voltage as in the prior-art apparatuses but using light.

Means to Solve the Objects

The inventor has found that if an ultra-narrow band light having a half bandwidth of 10 nm or less is diffused and projected to the face of a patient, light having a specific wavelength has an excellent hypnotic effect and has completed a sound sleep inducing apparatus according to the present invention. In this description, the light having the half bandwidth of 10 nm or less is referred to as ultra-narrow band light and is distinguished from single-color light of a usual LED (light emitting diode) (the half bandwidth is 20 to 40 nm). The half bandwidth refers to a width of a wavelength of light having intensity half of the center wavelength (peak wavelength) of a light source.

That is, in order to solve the above problems, a sound sleep inducing apparatus in a first aspect according to the present invention includes:

1-1) ultra-narrow band light projecting means which emits ultra-narrow band light in blue to green having a peak wavelength range of 430 to 550 nm and a half bandwidth of 10 nm or less;
1-2) diffusing means which diffuse an irradiation area of the light projected from the ultra-narrow band light projecting means to the entire face of a person; and
1-3) illuminance adjusting means which adjusts illuminance at a position of an eye in the face to 1 to 300 lux.

According to the above configuration, the light can be projected to the entire face of the subject, and an action to induce sleep or to awake can be exerted. The ultra-narrow band light having the half bandwidth of 10 nm or less has been in the laser state, and the laser beam has a defect that its brightness is too high to induce sleep. Thus, in the present invention, the ultra-narrow band light having the half bandwidth of 10 nm or less is passed through a concave lens and diffused. The green ultra-narrow band light having the half bandwidth of 10 nm or less has a sleep inducing effect, and the blue ultra-narrow band light has a particularly strong sleep inducing effect.

The illuminance adjusting means adjusts the illuminance at a position of an eye in the face to 1 to 300 lux. It was found by an experiment on a patient that adjustment to a range of 20 to 250 lux is particularly preferable. The illuminance adjusting means specifically adjusts light source intensity of the ultra-narrow band light projecting means, adjusts a diffusion degree of the diffusing means, and adjusts a distance between the light source of the ultra-narrow band light projecting means and the face. Moreover, the illuminance on the face surface may be measured by placing an illuminance sensor on the face surface or by measuring light reflected by a mirror placed on the face surface by using an illuminance sensor built in the ultra-narrow band light projecting means.

Moreover, a sound sleep inducing apparatus in a second aspect according to the present invention includes:

2-1) ultra-narrow band light projecting means which generates blue ultra-narrow band light having a peak wavelength range of 430 to 500 nm and a half bandwidth of 10 nm or less;
2-2) diffusing means which diffuses an irradiation area of the light projected from the ultra-narrow band light projecting means to the entire face of a person; and
2-3) illuminance adjusting means which adjusts illuminance at a position of an eye in the face to 1 to 300 lux.

According to the above configuration, a strong sleep inducing effect can be obtained. It was clinically demonstrated that a stronger sleep inducing effect can be obtained by irradiating the entire face with the blue ultra-narrow band light having the half bandwidth of 10 nm or less with a predetermined illuminance than irradiation of blue single light (half bandwidth of 20 to 40 nm) emitted by a usual LED light source. Specifically, 40 to 60 persons out of 100 subjects obtained a sleep inducing effect when blue single light (half bandwidth of 20 to 90 nm) was projected by a usual LED light source, while 80 persons or more obtained a sleep inducing effect if the blue ultra-narrow band light having the half bandwidth of 10 nm or less was projected to the eye position in the face with a predetermined illuminance. It was also found through the experiment that the blue light is preferably adjusted to a range of 20 to 120 lux.

Moreover, a sound sleep inducing apparatus in a third aspect according to the present invention includes:

3-1) ultra-narrow band light projecting means which generates green ultra-narrow band light having a peak wavelength range of 500 to 550 nm and a half bandwidth of 10 nm or less;
3-2) diffusing means which diffuse an irradiation area of the light projected from the ultra-narrow band light projecting means to the entire face of a person; and
3-3) illuminance adjusting means which adjusts illuminance at a position of an eye in the face to 1 to 300 lux.

According to the above configuration, a relaxing and gentle sleep inducing effect can be obtained. It was clinically demonstrated that an excellent sleep inducing effect can be obtained by irradiating the entire face with the green ultra-narrow band light having the half bandwidth of 10 nm or less with a predetermined illuminance than irradiation of green single light (half bandwidth of 20 to 40 nm) emitted by a usual LED light source. Specifically, not more than 40 persons out of 100 subjects obtained a sleep inducing effect when green single light (half bandwidth of 20 to 40 nm) was projected by an LED light source, while 60 persons or more obtained a sleep inducing effect if the green ultra-narrow band light having the half bandwidth of 10 nm or less was projected to the eye position in the face with a predetermined illuminance. It was also found through the experiment that blue light is preferably adjusted to a range of 50 to 250 lux.

Moreover, in the sound sleep inducing apparatus in the first aspect according to the present invention, the ultra-narrow band light projecting means further includes first ultra-narrow band light projecting means which generates blue ultra-narrow band light having a peak wavelength range of 430 to 500 nm and a half bandwidth of 10 nm or less, second ultra-narrow band light projecting means which generates green ultra-narrow band light having a peak wavelength range of 500 to 550 nm and a half bandwidth of 10 nm or less, light-source switching means which switches between the first ultra-narrow band light projecting means and the second ultra-narrow band light projecting means, and control means which outputs a switching signal to the light-source switching means.

According to the above configuration, sleep induction can be gently performed by alternately using the blue ultra-narrow band light having a strong sleep inducing effect and the green ultra-narrow band light having a relaxing and sleep inducing effect. The control means preferably outputs output signals alternately to the first ultra-narrow band light projecting means and the second ultra-narrow band light projecting means with a predetermined time interval, since deep sleep is induced by alternately irradiating the entire face with the green and blue lights from the respective LEDs. The predetermined time is approximately 1 minute, and the sleep inducing effect is exerted in approximately 10 minutes.

In this case, the illuminance adjusting means preferably adjusts the illuminance at the eye position in the face to 20 to 120 lux for the projection from the first ultra-narrow band light projecting means and to 50 to 250 lux for the projection from the second ultra-narrow band light projecting means. Each color has its own optimal illuminance, and the illuminance is adjusted in accordance with switching of colors.

Moreover, in the sound sleep inducing apparatus in the first to third aspects, the half bandwidth of the ultra-narrow band light projecting means is more preferably 3 nm or less. Projection of the ultra-narrow band light having the half bandwidth of 3 nm or less by using a bandpass filter with a narrower area than projection of the ultra-narrow band light having the half bandwidth of 10 nm or less was found to obtain a higher sleep inducing effect from experiments.

Moreover, in the sound sleep inducing apparatus in the first to third aspects, energy at the irradiated portion in the human face is set to 1.0 J/cm$^2$ or less. Laser beam has high energy, but the recent progress of LED has achieved higher irradiation energy. In the sound sleep inducing apparatus in the first to third aspects, the energy at the irradiated portion in the human face is set to 1.0 J/cm$^2$ or less. The irradiation time is 5 to 15 minutes and approximately 30 minutes at the longest.

Moreover, in the sound sleep inducing apparatus in the first to third aspects, the ultra-narrow band light projecting means is specifically composed of an LED light source and a bandpass filter which narrows the wavelength band of the light emitted from the LED light source. Even if an LED light source capable of projecting the ultra-narrow band light having the half bandwidth of 10 nm or less is developed in the future, the ultra-narrow band light having further narrower half bandwidth can be created by the above configuration of the ultra-narrow band light projecting means, that is, the configuration of the LED light source and the bandpass filter.

Moreover, in the sound sleep inducing apparatus in the first to third aspects, the diffusing means is specifically composed of at least any one of a concave lens, a diffusing lens, a cylindrical lens and a diffusing plate. Among them, a diffusing lens can be suitably used from the viewpoint of minimizing attenuation of a light amount.

Moreover, if a cylindrical lens is used as the diffusing means, two cylindrical lenses are arranged in directions orthogonal to each other in use. In general, a cylindrical lens is used in an application requiring magnification adjustment only in one direction and forms an image only in one direction, but since the same image forming formula as a spherical lens is true for the cylindrical lens, the first cylindrical lens collimates the beam in one direction and the second cylindrical lens collimates the beam also in the direction orthogonal to that in use. A diffusing lens or a diffusion plate may be used at the same time with the cylindrical lens used as the diffusing means.

The sound sleep inducing apparatus of the present invention can be suitably used as lighting fixture or particularly as a desk light. It may be also mounted on a bed. The sound sleep inducing apparatus of the present invention is suitably used at hospitals and households. That is, the sound sleep inducing apparatus of the present invention may be used for lighting of a hospital room, and illuminance close to the face of a patient lying on the bed is adjusted and the patient is induced to sound sleep after the bedtime. By projecting the blue to green light without turning off the light at the bedtime, the periphery of the bed can be seen better and safety is improved. If the apparatus is mounted on the bed, the projection range of the ultra-narrow band light can be controlled by a housing of the ultra-narrow band light projecting means similarly to a usual desk light. A patient can be induced to sound sleep even when the light is on or during bright daytime by irradiating only to the face portion of the patient.

Subsequently, a sound sleep inducing method of the present invention will be described. The sound sleep inducing method of the present invention is to diffuse and project ultra-narrow band light in blue to green having a peak wavelength range of 430 to 550 nm and a half bandwidth of 10 nm or less to the entire face of a person and to adjust illuminance at an eye position of the face to 20 to 250 lux. According to this method, an excellent sound sleep inducing effect can be obtained.

Moreover, in the sound sleep inducing method of the present invention, the light is blue light having a peak wavelength range of 430 to 550 nm and a half bandwidth of 10 nm or less, and its illuminance at the eye position in the face is preferably adjusted to 20 to 120 lux. A strong sleep inducing effect can be obtained by the blue light having the half bandwidth of 10 nm or less.

Moreover, in the sound sleep inducing method of the present invention, the light is green light having a peak wavelength range of 500 to 550 nm and a half bandwidth of 10 nm or less, and its illuminance at the eye position in the face is preferably adjusted to 50 to 250 lux. A relaxing and gentle sleep inducing effect can be obtained by the green light having the half bandwidth of 10 nm or less.

Moreover, according to the sound sleep inducing method of the present invention, the ultra-narrow band light is projected by switching between the following first ultra-narrow band light and second ultra-narrow band light, and in projection of the first ultra-narrow band light, the illuminance at the eye position in the face is adjusted to 20 to 120 lux, while in projection of the second ultra-narrow band light, the illuminance is adjusted to 50 to 250 lux. The first ultra-narrow band light is blue ultra-narrow band light having a peak wavelength range of 430 to 500 nm and a half bandwidth of 10 nm or less, while the second ultra-narrow band light is green ultra-narrow band light having a peak wavelength range of 500 to 550 nm and a half bandwidth of 10 nm or less. According to this method, sleep induction can be gently performed by alternately using the blue ultra-narrow band light having a strong sleep inducing effect and the green ultra-narrow band light having a relaxing and sleep inducing effect.

In the sound sleep inducing method of the present invention, the half bandwidth of the ultra-narrow band light is more preferably 3 nm or less. Projection of the ultra-narrow band light having the half bandwidth of 3 nm or less has more excellent sleep inducing effect than projection of the ultra-narrow band light having the half bandwidth of 10 nm or less.

Effects of the Invention

According to the sound sleep inducing apparatus and the sound sleep inducing method of the present invention, an effect of promoting comfortable sound sleep without giving a sense of psychological limitation or isolation can be obtained.

BEST MODE FOR CARRYING OUT THE INVENTION

Hereinafter, an embodiment of the present invention will be described with reference to the accompanying drawings. The present invention is not limited to the illustrated construction. The present invention can be variously changed in design.

Figure 1:
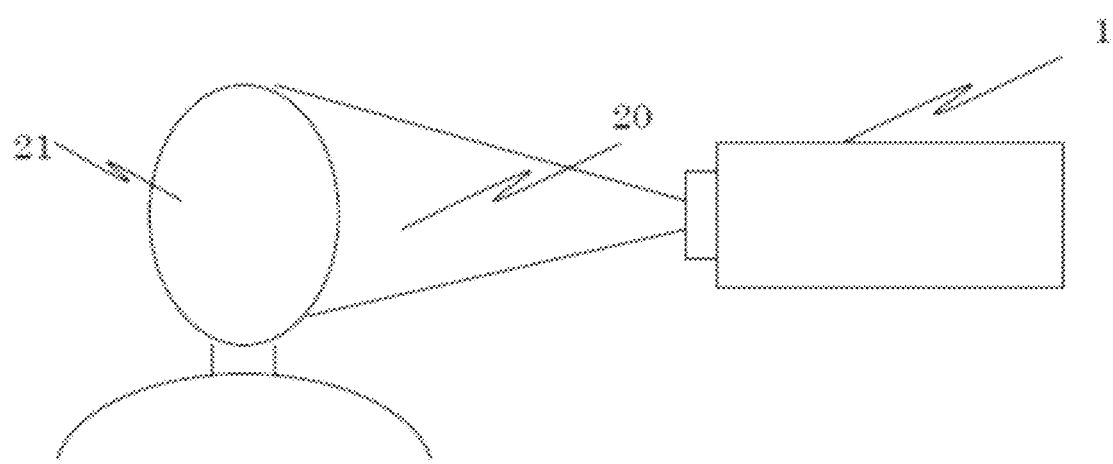
FIG. 1 is a used image diagram of the sound sleep inducing apparatus.

FIG. 1 illustrates a used image diagram of the sound sleep inducing apparatus. A sound sleep inducing apparatus 1 induces sleep by irradiating the entirety of a face 21 of a person with ultra-narrow band light 20 in blue to green having a specific wavelength in a predetermined illuminance range.

Figure 2:
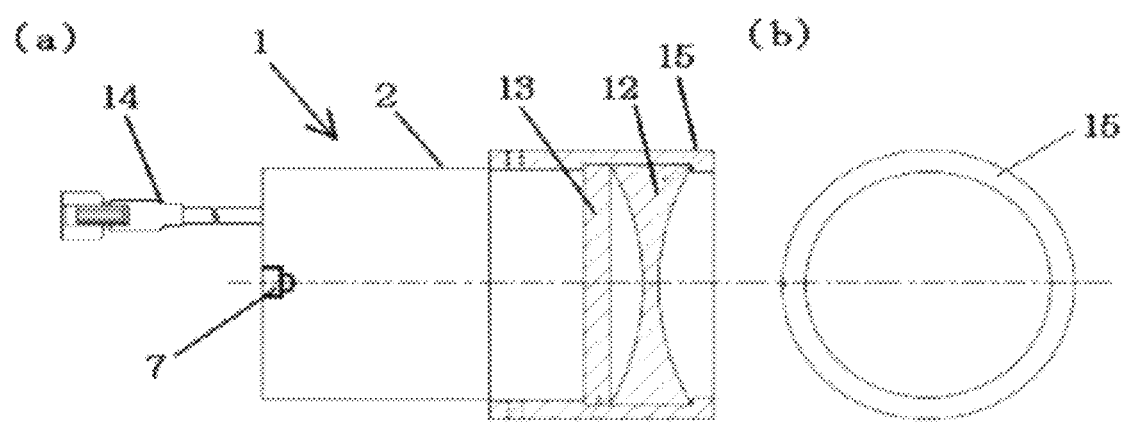
FIG. 2 is a configuration diagram of the sound sleep inducing apparatus.

FIG. 2 illustrates a configuration diagram of an embodiment of the sound sleep inducing apparatus. The sound sleep inducing apparatus 1 includes a blue or green LED light source 7 having a half bandwidth of 20 to 40 nm mounted on the bottom part of a cylindrical main body 2, a bandpass filter 13 which narrows a wavelength band of light emitted from the LED light source 7, and a diffusing lens 12 which diffuses light in an ultra-narrow band area passing through the bandpass filter 13 and having a half bandwidth of 10 nm or less. An ON/OFF signal and power of the LED light source 7 is supplied through a signal/power cable 14. The bandpass filter 13 and the diffusing lens 12 are mounted on a housing frame 15 and are detachably attached to the cylindrical main body 2. Light in an ultra-narrow band area having a desired half bandwidth can be created by replacing the bandpass filter 13. An irradiation area can be adjusted by replacing the diffusing lens 12.

As the LED light source 7, a parallel-light LED light source (model number: IBF-LS) by IMAC Co., Ltd. can be used. The light emitted from the LED light source 7 is ultra-long cast directive light. The inner diameter of the cylindrical main body 2, that is, a photo diameter of the parallel-light LED light source is approximately 5 cm, and this light is diffused by the diffusing lens 12.

In the sound sleep inducing apparatus 1, as means for adjusting the illuminance of light in the ultra-narrow band area to be projected to a human face, intensity of the light source of the ultra-narrow band light inside the sound sleep inducing apparatus 1 is adjusted by placing an illuminometer beside the eyes of the human face 21 or by replacing the diffusing lens in the sound sleep inducing apparatus 1.

It is also possible to incorporate an illuminance sensor in the sound sleep inducing apparatus 1, to place a mirror on the surface of the face, and by having the light reflected by the mirror measured by the illuminance sensor incorporated in the sound sleep inducing apparatus 1 so that the intensity of the ultra-narrow band light in the light source is automatically adjusted. The illuminometer used for the measurement of the embodiment described below is a TOPCOM (registered trademark) illuminometer IM-5.

Figure 3:
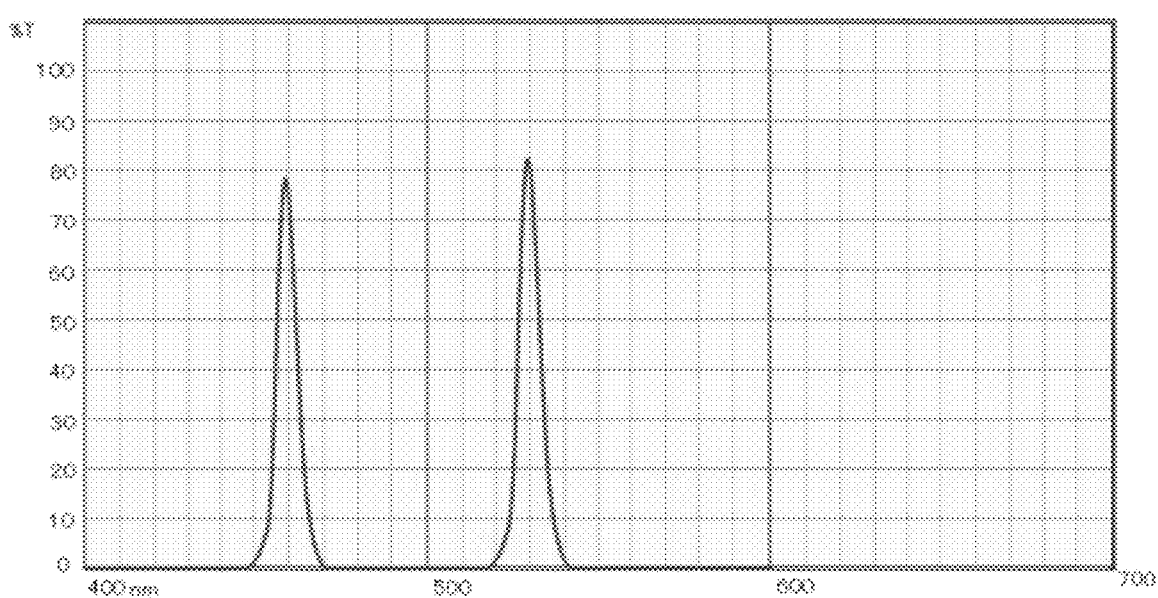
FIG. 3 is an example of spectrum of the ultra-narrow band light emitted from the sound sleep inducing apparatus.

FIG. 3 illustrates an example of spectrum of the ultra-narrow band light emitted from the sound sleep inducing apparatus 1. The lateral axis indicates a wavelength and the vertical axis for intensity. The blue ultra-narrow band light has a center wavelength (peak wavelength) at 460 nm and a half bandwidth at 10 nm. The green ultra-narrow band light has a center wavelength (peak wavelength) at 530 nm and a half bandwidth at 10 nm.

Embodiment 1

In Example 1, the excellent sleep inducing effect of the sound sleep inducing apparatus will be provided, including:

1-1) ultra-narrow band light projecting means which generates blue to green ultra-narrow band light having a peak wavelength range of 430 to 550 nm and a half bandwidth of 10 nm or less;
1-2) diffusing means which diffuses an irradiation area of the light projected from the ultra-narrow band light projecting means to the entire face of a person; and
1-3) illuminance adjusting means which adjusts illuminance at an eye position of the face to 1 to 300 lux.

A clinical experiment was actually conducted for verifying the sleep inducing effect by using the sound sleep inducing apparatus for 100 subjects including men and women with the ages of 20 to 70. The ratio of men to women was 30:70. The ratio of women is higher simply because our clinic is specialized in cosmetic treatment and it does not have a special meaning. The ages of the subjects were 35 people in the 20's, 25 people in the 30's, 2.5 people in the 40's, and 15 people in the 50 to 60's. An example which will be described later was also conducted for the same subjects. The sleep inducing effect as indicated in Table 1 was obtained. In the Table, the number of those with a poor result was less than 40, those with fair was 40 to 59, these with good was 60 to 79, and those with very good was 80 or more.

The result No. 1 in Table was obtained from determination of the sleep inducing effect by using some commercial LED light sources, each having a center wavelength (peak wavelength) in a range of 430 to 550 nm. In the case of the commercial LED light sources, the half bandwidth was varied from 15 to 40 nm. The LED light source was brought close to the face so as to obtain the illuminance at the eye position in the face of 1 to 450 lux, and the sleep inducing effect was determined. The result No. 2 in Table was obtained by using the No. 1 LED light source and configuring the sound sleep inducing apparatus configured as in FIG. 2. The light of the LED light source was set to the half bandwidth at 10 nm by using a bandpass filter. The sleep inducing effect was determined by bringing the LED light source close to the face to obtain the illuminance at the eye position in the face larger than 300 lux. The result No. 3 in Table was obtained by using the LED light source in No. 2, by configuring the sound sleep inducing apparatus configured as in FIG. 2, and by using the diffusing lens to adjust the illuminance at the eye position in the face to 1 to 300 lux.

The result No. 10 is obtained by determining the sleep inducing effect by using some commercial LED light sources having the center wavelength (peak wavelength) outside the range of 430 to 550 nm. Specifically, the sleep inducing effect was determined by using the LED light source (half bandwidth at 35 nm) having the center wavelength (peak wavelength) at 405 nm and the LED light source (half bandwidth at 25 nm) having the center wavelength at 570 nm.

TABLE 1

| No. | | Determination of the sleep inducing effect |
|---|---|---|
| 1 | LED having a peak wavelength of 430 to 550 nm | fair |
| 2 | No. 1 LED having the half bandwidth of 10 nm or less | good |
| 3 | No. 2 LED having illuminance at the eye position in the face adjusted to 1 to 300 lux | very good |
| 10 | LED having the peak wavelength of 405 nm or 570 nm | poor |

Embodiment 2

Subsequently, in Example 2, the excellent sleep inducing effect of the sound sleep inducing apparatus will be described, including:
2-1) ultra-narrow band light projecting means which generates blue ultra-narrow band light having a peak wavelength range of 430 to 500 nm and a half bandwidth of 10 nm or less;
2-2) diffusing means which diffuses an irradiation area of the light projected from the ultra-narrow band light projecting means to the entire face of a person; and
2-3) illuminance adjusting means which adjusts illuminance at an eye position of the face to 1 to 300 lux.

A clinical test was conducted by actually using the sound sleep inducing apparatus, and the sleep inducing effect as illustrated in Table 2 was obtained.

TABLE 2

| No. | | Determination of the sleep inducing effect |
|---|---|---|
| 4 | Blue LED having a peak wavelength of 430 to 550 nm | fair |
| 5 | No. 4 Blue LED having the half bandwidth of 10 nm or less | good |
| 6 | No. 5 Blue LED having illuminance at the eye position in the face adjusted to 1 to 300 lux | very good |

Embodiment 3

Subsequently, in Example 3, the excellent sleep inducing effect of the sound sleep inducing apparatus will be described, including:
3-1) ultra-narrow band light projecting means which generates green ultra-narrow band light having a peak wavelength range of 500 to 530 nm and a half bandwidth of 10 nm or less;
3-2) diffusing means which diffuses an irradiation area of the light projected from the ultra-narrow band light projecting means to the entire face of a person; and
3-3) illuminance adjusting means which adjusts illuminance at an eye position of the face to 1 to 300 lux.

A clinical experiment was conducted by actually using the sound sleep inducing apparatus, and the sleep inducing effect as illustrated in Table 3 was obtained.

TABLE 3

| No. | | Determination of the sleep inducing effect |
|---|---|---|
| 7 | Green LED having a peak wavelength of 500 to 550 nm | fair |
| 8 | No. 7 Green LED having the half bandwidth of 10 nm or less | good |
| 9 | No. 8 Green LED having illuminance at the eye position in the face adjusted to 1 to 300 lux | very good |

Experiment data used for determination of the sleep inducing effect in Tables 1 to 3 is illustrated in Table 4. Each No. here corresponds to No. in Tables 1 to 3.

TABLE 4

| | 20's | | 30's | | 40's | | 50 to 60's | | Total | |
|---|---|---|---|---|---|---|---|---|---|---|
| No. | Effective | Non-effective | Effective | Non-effective | Effective | Non-effective | Effective | Non-effective | Effective | Non-effective |
| 1 | 16 | 19 | 9 | 16 | 10 | 15 | 7 | 8 | 42 | 58 |
| 2 | 24 | 11 | 16 | 9 | 15 | 10 | 11 | 4 | 66 | 34 |
| 3 | 32 | 3 | 21 | 4 | 21 | 4 | 13 | 2 | 87 | 13 |
| 4 | 19 | 16 | 11 | 14 | 12 | 13 | 9 | 6 | 51 | 49 |
| 5 | 26 | 9 | 19 | 6 | 18 | 7 | 12 | 3 | 75 | 25 |
| 6 | 34 | 1 | 22 | 3 | 22 | 3 | 14 | 1 | 92 | 8 |
| 7 | 6 | 29 | 4 | 21 | 5 | 20 | 3 | 12 | 18 | 82 |
| 8 | 18 | 17 | 10 | 15 | 11 | 14 | 5 | 10 | 44 | 56 |
| 9 | 22 | 13 | 16 | 9 | 17 | 8 | 9 | 6 | 64 | 36 |
| 10 | 5 | 30 | 4 | 21 | 5 | 20 | 1 | 14 | 15 | 85 |

The 1.0.0 subjects of men and women in their 20's to 70's include 15 insomnia monitors. The insomnia monitors refer to those who need sleeping pills when going to bed at night. The 15 insomnia monitors are 5 men and 10 women and are composed of 2 men and 4 women in the 20's, 1 man and 3 women in the 30's, 1 man and 2 women in the 40's, and 1 man and 1 woman in the 50 to 60's. The insomnia monitors are found to have obtained the 100.% effect in No. 3, No, 6, and No. 9.

Embodiment 4

In Example 4, the result of examination of a suitable value of illuminance at the eye position in the face by using the ultra-narrow band light (No. 3, No. 6, and No. 9) having the half bandwidth of 10 nm in Examples 1, 2, and 3 is shown. In the ultra-narrow band light (No. 3, No. 6, and No. 9) having the half bandwidth of 10 nm in Examples 1, 2, and 3, the illuminance at the eye position in the face was set to 1, 15, 20, 50, 80, 120, 125, 250, 300, 330 (lux), and the experiment was conducted. The result of the sleep inducing effect as illustrated in Table 5 was obtained. In Table, those with a fair result were 40 to 59 persons, those with good were 60 to 79 persons, those with very good were 80 to 92 persons, and those with NA were 93 persons or more.

TABLE 5

| No. | 1 | 15 | 20 | 50 | 80 | 120 | 125 | 250 | 300 | 330 |
|---|---|---|---|---|---|---|---|---|---|---|
| 3 | good | good | very good | NA | NA | NA | NA | very good | good | faire |
| 6 | good | good | very good | NA | NA | very good | good | good | good | faire |
| 9 | good | good | good | very good | NA | NA | NA | very good | good | faire |

Embodiment 5

In Example 5, the fact that the ultra-narrow band light having the half bandwidth of 3 nm had a better sleep inducing effect than the ultra-narrow band light having the half bandwidth of 10 nm in Examples 1, 2, and 3 (No. 3, No, 6, and No. 9) will be described. The ultra-narrow band light having the half bandwidth of 3 nm was realized by replacing the bandpass filter.

A clinical test was conducted by actually using the sound sleep inducing apparatus of the ultra-narrow band light having the half bandwidth of 3 nm and the apparatus having the half bandwidth of 10 nm, and the result of the sleep inducing effect as illustrated in Table 6 was obtained. Nos. in Table 6 correspond to Nos. in Tables 1 to 3. The numerical values in Table indicate the number of monitors with the higher sleep inducing effect by using the sound sleep inducing apparatus of the ultra-narrow band light having the half bandwidth of 3 nm than the apparatus having the half bandwidth of 10 nm in the 100 monitors and those with the higher sleep inducing effect by using the sound sleep inducing apparatus of the ultra-narrow band light having the half bandwidth of 10 nm than the apparatus having the half bandwidth of 3 nm.

As illustrated in Table 6, 80% or more of the monitors obtained the higher sleep inducing effect by using the sound sleep inducing apparatus of the ultra-narrow band light having the half bandwidth of 3 nm than the apparatus having the half bandwidth of 10 nm. The conditions other than the half bandwidth are the same.

TABLE 6

| | 20's | | 30's | | 40's | | 50 to 60's | | Total | |
|---|---|---|---|---|---|---|---|---|---|---|
| No. | 3 nm | 10 nm | 3 nm | 10 nm | 3 nm | 10 nm | 3 nm | 10 nm | 3 nm | 10 nm |
| 3 | 29 | 6 | 22 | 3 | 21 | 4 | 13 | 2 | 85 | 15 |
| 6 | 30 | 5 | 21 | 4 | 22 | 3 | 13 | 2 | 84 | 14 |
| 9 | 28 | 7 | 21 | 4 | 20 | 5 | 12 | 3 | 81 | 19 |

INDUSTRIAL APPLICABILITY

The present invention is useful as an apparatus and a Method for promoting sleep.

[Description of Symbols]
1. Sound sleep inducing apparatus
2. Cylindrical main body
7. LED light source
12. Diffusing lens
13. Bandpass filter
14. Signal/Power cable
15. Housing frame
20. Person with ultra-narrow band light
21. Human face

What is claimed is:

1. A sound sleep inducing method characterized in that:
projecting ultra-narrow band light in blue having a peak wavelength range of 450 to 470 nm and a half bandwidth of 3 nm or less to an entire face of a person with illuminance at an eye position in the face being 20 to 120 lux;
controlling an irradiation energy of the light in blue at an irradiated portion in the face to be less than 1.0 J/cm$^2$; and
controlling an irradiation time in the light in blue to be from 5 to 15 minutes.

2. The method of claim 1, wherein said ultra-narrow band light in blue has a peak wavelength of 460 nm.

3. A sound sleep inducing apparatus comprising:
an ultra-narrow band light source which generates blue ultra-narrow band light having a peak wavelength range of 450 to 470 nm and a half bandwidth of 3 nm or less; and
diffusing and illuminance adjusting means which diffuses an irradiation area of the light projected from the ultra-narrow band light source to at least a portion of a face of a person and which adjusts illuminance at a position of an eye in the face from 20 to 120 lux,
wherein the apparatus controls an irradiation energy of the light in blue at an irradiated portion in the face by less than 1.0 J/cm$^2$, an irradiation time of the light in blue to be from 5 to 15 minutes.

4. The apparatus of claim 3, wherein said ultra-narrow band light in blue has a peak wavelength of 460 nm.

5. The apparatus of claim 3, wherein said ultra-narrow band light source comprises an LED light source and a bandpass filter.

6. The apparatus of claim 3, wherein said ultra-narrow band light source comprises an LED light source capable of projecting the ultra-narrow band light having the half bandwidth of 3 nm or less.

7. A sound sleep inducing method comprising:
diffusing ultra-narrow band light in blue having a peak wavelength in a range of 450 to 470 nm and a half bandwidth of 3 nm or less; and
projecting at least a portion of said ultra-narrow band light in blue to an entire face of a person while illuminance at an eye position in the face is 20 to 120 lux, without projecting light having a peak wavelength of 570 nm.

8. The method of claim 7, wherein said ultra-narrow band light in blue has a peak wavelength of 460 nm.

9. The method of claim 7, further comprising controlling an irradiation time in the light in blue to be from 5 to 30 minutes.

10. The method of claim 7, further comprising controlling an irradiation time in the light in blue to be from 5 to 15 minutes.

* * * * *